US010647942B2

(12) United States Patent
Blandino et al.

(10) Patent No.: US 10,647,942 B2
(45) Date of Patent: May 12, 2020

(54) FRAGRANCE AND FLAVOR MATERIALS

(71) Applicant: TAKASAGO INTERNATIONAL CORPORATION, Tokyo (JP)

(72) Inventors: Maureen Blandino, Dumont, NJ (US); Michael E. Lankin, High Bridge, NJ (US)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 0 days.

(21) Appl. No.: 16/466,107

(22) PCT Filed: Dec. 22, 2017

(86) PCT No.: PCT/US2017/068357
§ 371 (c)(1),
(2) Date: Jun. 3, 2019

(87) PCT Pub. No.: WO2018/119466
PCT Pub. Date: Jun. 28, 2018

(65) Prior Publication Data
US 2020/0063062 A1     Feb. 27, 2020

Related U.S. Application Data

(60) Provisional application No. 62/438,374, filed on Dec. 22, 2016.

(51) Int. Cl.
| | |
|---|---|
| *C11B 9/00* | (2006.01) |
| *C07C 47/21* | (2006.01) |
| *C07C 69/533* | (2006.01) |
| *C07C 251/40* | (2006.01) |
| *C07C 229/30* | (2006.01) |
| *C07C 33/025* | (2006.01) |
| *C07C 255/07* | (2006.01) |
| *A23L 27/20* | (2016.01) |

(52) U.S. Cl.
CPC ........ *C11B 9/0015* (2013.01); *A23L 27/2024* (2016.08); *C07C 33/025* (2013.01); *C07C 47/21* (2013.01); *C07C 69/533* (2013.01); *C07C 229/30* (2013.01); *C07C 251/40* (2013.01); *C07C 255/07* (2013.01); *C11B 9/0007* (2013.01); *C11B 9/0019* (2013.01); *C11B 9/0023* (2013.01); *A23V 2002/00* (2013.01)

(58) Field of Classification Search
CPC ...... C11B 9/0015; C11B 9/0023; C07C 47/21
See application file for complete search history.

(56) References Cited

U.S. PATENT DOCUMENTS 7,544,647 B1     6/2009 Narula et al.

FOREIGN PATENT DOCUMENTS

| GB | 1281813 A | 7/1972 |
|---|---|---|
| WO | WO 2016/091895 A1 | 6/2016 |

OTHER PUBLICATIONS

U.S. Appl. No. 16/466,084, filed Jun. 3, 2019.
U.S. Appl. No. 16/466,080, filed Jun. 3, 2019.
Chan et al., "Synthetic Studies on (2R,4'R,8'R)-a-Tocopherol. Facile Syntheses of Optically Active, Saturated, Acyclic Isoprenoids via Stereospecific [3,3] Sigmatropic Rearrangements," J. Org. Chem 41(22):3497-3505 (1976).
International Search Report dated Mar. 19, 2018 in International Application No. PCT/US2017/068363.
International Search Report dated Mar. 20, 2018 in International Application No. PCT/US2017/068361.
International Search Report dated Mar. 27, 2018 in International Application No. PCT/US2017/068357.
Liapis et al., "Improved Total Synthesis of (+)-Drimenin," J. Chem Soc Perkin Trans I pp. 815-817 (1985).
Mori et al., "A Synthesis of dl-C17-Cecropia Juvenile Hormone," Agricultural and Biological Chemistry, 36(11):1931-1936 (1972).
Nazarov et al., "Synthesis of Higher Fatty Acids and Alcohols from Tertiary Vinyl Carbinols," Moscow Institute of Fine Chemical Engineering, 30:443-450 (Jan. 1, 1960) (with English translation).
Nowicki, "Claisen, Cope and Related Rearrangements in the Synthesis of Flavour and Fragrance Compounds," Molecules 5:1033-1050 (2000).
S. Arctander, Perfume and Flavor Chemicals, 1969, vols. 1 and 2, Table of Contents.
Wei et al., "Tandem Pd(II)-Catalyzed Vinyl Ether Exchange-Claisen Rearrangement as a Facile Approach to γ,δ-Unsaturated Aldehydes," J. Org. Chem. 72:4250-4253 (2007).
Winska et al., "Synthesis and odour characteristics of racemic and optically active oxy-derivatives of gem-dimethylcyclohexene," Flavour Fragr. J. 26:329-335 (2011).

*Primary Examiner* — Karen Cheng
(74) *Attorney, Agent, or Firm* — Baker Botts L.L.P.

(57) ABSTRACT

The present disclosure is directed to the synthesis and application of undecavertol derivatives having unique and desired flavor and/or fragrant characteristics. The compounds of the present disclosure can be employed alone or incorporated as fragrance or flavor ingredients in fragrance or flavor compositions. The present disclosure is also directed to consumer products comprising such derivatives and/or fragrance or flavor compositions.

9 Claims, No Drawings

FRAGRANCE AND FLAVOR MATERIALS

CROSS-REFERENCE TO RELATED APPLICATIONS

The present application is a U.S. National Stage Patent Application under 35 U.S.C. § 371 of International Application No. PCT/US2017/068357, filed on Dec. 22, 2017, which claims priority to U.S. Provisional Application No. 62/438,374, filed on Dec. 22, 2016, the contents of each of which are incorporated herein by reference in its their entirety.

FIELD OF THE INVENTION

The present application relates to compounds useful as fragrance or flavor components in fragrance or flavor compositions.

BACKGROUND OF THE INVENTION

There is a continuing interest in the preparation of synthetic fragrance and flavor components and their use in consumer products. One strategy to prepare such compounds is to apply a known synthetic chemical reaction to readily available substrates. The Claisen Rearrangement is a reaction known to one skilled in the art of organic synthesis. When an allylic alcohol is converted to the vinyl ether and treated with acid and heat, the vinyl ether rearranges to a 4-alkenal. There are several Claisen products known for their use in the flavor and fragrance industry (Nowicki, Molecules 2000, 1033-1050). A similar rearrangement is the Johnson Rearrangement, also known to one skilled in the art, whereby an allylic alcohol is converted to a 4-alkenoic ester.

There remains a need and demand for unique fragrance and flavor compounds. There is also a need for fragrance and flavor compositions with pleasing and consumer preferred odor and taste profiles for use in multiple consumer products.

SUMMARY OF THE INVENTION

The present disclosure is directed to the synthesis and application of undecavertol derivatives having unique and desired flavor and/or fragrant characteristics. The compounds of the present disclosure can be employed alone or incorporated as fragrance or flavor compositions.

In certain embodiments, the presently disclosed subject matter provides compounds of the Formula (I),

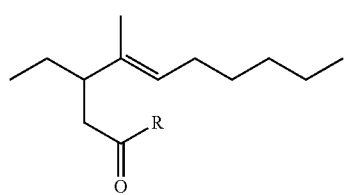

(I)

In certain embodiments, R is hydrogen, a hydroxy group, or a $C_{1-2}$ alkoxy group.

In certain embodiments, the presently disclosed subject matter provides compounds of the Formula (II),

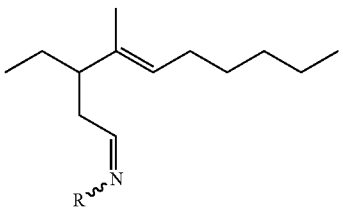

(II)

In certain embodiments, R is a hydroxy group, a $C_{1-2}$ alkoxy group, an acetoxy group, 2-methylbenzoyl, or 2-ethylbenzoyl.

In certain embodiments, the presently disclosed subject matter provides compounds of the Formula (III),

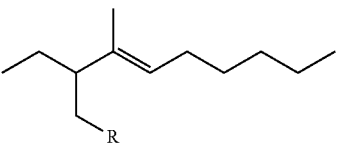

(III)

In certain embodiments, R is a hydroxymethyl group, a methyl ethanoate group, 1-ethanol, or a cyano group.

In certain embodiments, the presently disclosed subject matter provides compounds of the Formula (IV),

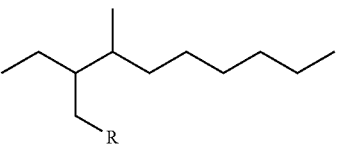

(IV)

In certain embodiments, R is a hydroxymethyl group or an aldehyde group.

In certain embodiments, the compounds include constitutional isomers, enantiomers, stereoisomers, and racemic mixtures of said compounds listed herein.

Another aspect of the present disclosure provides a fragrance or flavor composition for addition to a consumer product comprising one or more compounds of Formulas (I-IV) in an amount effective to impart a fragrance or flavor to the consumer product.

DETAILED DESCRIPTION

Definitions

The terms used in this specification generally have their ordinary meanings in the art, within the context of this disclosure and in the specific context where each term is used. Certain terms are discussed below, or elsewhere in the specification, to provide additional guidance to a person of ordinary skill in the art describing the compositions and methods of the disclosure and how to make and use them.

As used herein, the use of the word "a" or "an" when used in conjunction with the term "comprising" in the claims and/or the specification can mean "one," but it is also consistent with the meaning of "one or more," "at least one," a plurality, and "one or more than one." Still further, the terms "having," "including," "containing" and "comprising"

are interchangeable and one of skill in the art is cognizant that these terms are open ended terms.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, the term "enantiomers" refers to a pair of stereoisomers that are non-superimposable mirror images of each other. A 1:1 mixture of a pair of enantiomers is a "racemic" mixture. The term is used to designate a racemic mixture where appropriate.

As used herein, the term "diastereoisomers" refers to stereoisomers that have at least two asymmetric atoms, but which are not mirror-images of each other. The absolute stereochemistry is specified according to the Cahn-Ingold-Prelog R-S system. When a compound is a pure enantiomer, the stereochemistry at each chiral carbon may be specified by either R or S. Resolved compounds whose absolute configuration is unknown can be designated (+) or (−) depending on the direction (dextro or levorotatory) which they rotate plane polarized light at the wavelength of the sodium D line. The compounds of the presently disclosed subject matter contain one or more asymmetric centers and may thus give rise to enantiomers, diastereomers, and other stereoisomeric forms that may be defined, in terms of absolute stereochemistry, as (R)- or (S)-. The presently disclosed subject matter is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. All tautomeric forms are also intended to be included.

As used herein, the term "isomers" refers to different compounds that have the same molecular formula but differ in arrangement and configuration of the atoms. Also as used herein, the term "stereoisomer" refers to any of the various stereo isomeric configurations which may exist for a given compound of the presently disclosed subject matter and includes geometric isomers. It is understood that a substituent may be attached at a chiral center of a carbon atom. Therefore, the presently disclosed subject matter includes enantiomers, diastereomers or racemates of the compound. Also as used herein, the terms "constitutional isomers" refers to different compounds which have the same numbers of, and types of, atoms but the atoms are connected differently.

As used herein, the term "fragrance composition" refers to a mixture comprising one or more fragrance components, in any of their forms, and one or more solvents or perfuming co-ingredients. As known in the art, a fragrance composition contains one or more fragrance components (e.g., perfuming co-ingredients) in order to impart an olfactory note to the composition (e.g., a household cleaner, perfume, or other consumer product) to which it is added. In one embodiment, the fragrance composition contains two or more fragrance components which, collectively and in combination with the solvent to which they are added, impart an intended olfactory note (e.g., a hedonically pleasing "tropical" note) to a human in close proximity to the fragrance composition.

In general terms, perfuming co-ingredients belong to chemical classes as varied as alcohols, aldehydes, ketones, esters, ethers, acetates, nitriles, terpene hydrocarbons, nitrogenous or sulphurous heterocyclic compounds, and essential oils of natural or synthetic origin, and are known to perfumists of ordinary skill in the art. Many of these ingredients are listed in reference texts such as S. Arctander, *Perfume and Flavor Chemicals,* 1969, Montclair, N.J., USA or any of its more recent versions, each of which are hereby incorporated by reference.

As used herein, the term "flavor composition" refers to a composition that contains one or more compounds (e.g., co-ingredients) that provide a desired taste when combined with a solvent that is suitable for oral administration and oral consumption. Examples of flavoring co-ingredients that are generally included in a flavor composition are listed in S. Arctander, *Perfume and Flavor Chemicals,* 1969, Montclair, N.J., USA. The skilled person in the art of flavors is able to select them on the basis of its general knowledge and according to the nature of the product to be flavored and the desired taste.

As used herein, the phrase "consumer product" or "end product" refers to composition that is in a form ready for use by the consumer for the marketed indication. A solvent suitable for use in a consumer product is a solvent that, when combined with other components of the end product, will not render the consumer product unfit for its intended consumer use.

Undecavertol Derivatives

The present disclosure is directed to the synthesis and application of undecavertol derivatives having unique and desired flavor and/or fragrant characteristics.

In certain embodiments, the presently disclosed subject matter provides compounds of the Formula (I),

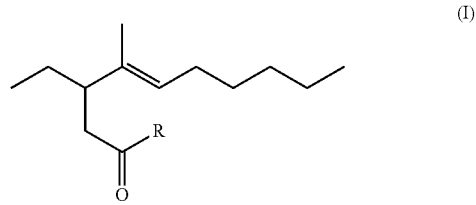

In certain embodiments, R is hydrogen, a hydroxy group, or a $C_{1-2}$ alkoxy group.

In certain embodiments, the presently disclosed subject matter provides compounds of the Formula (II),

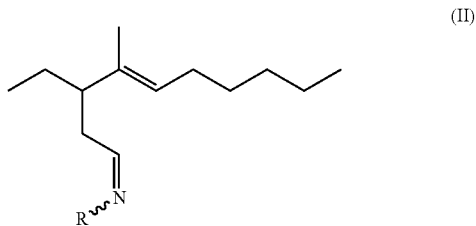

In certain embodiments, R is a hydroxy group, a $C_{1-2}$ alkoxy group, an acetoxy group, 2-methylbenzoyl, or 2-ethylbenzoyl.

In certain embodiments, the presently disclosed subject matter provides compounds of the Formula (III),

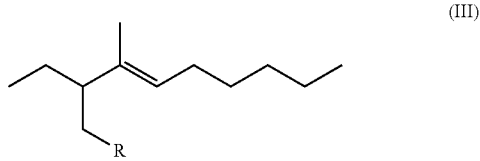

(III)

In certain embodiments, R is a hydroxymethyl group, a methyl ethanoate group, 1-ethanol, or a cyano group.

In certain embodiments, the presently disclosed subject matter provides compounds of the Formula (IV),

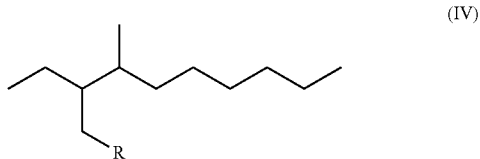

(IV)

In certain embodiments, R is a hydroxymethyl group or an aldehyde group.

In certain embodiments, the compounds include constitutional isomers, enantiomers, stereoisomers, and racemic mixtures of said compounds listed herein.

The compounds of the present disclosure can be prepared synthetically. In certain embodiments, the compounds of the present disclosure are prepared by a Claisen Rearrangement of undecavertol. In certain embodiments, the compounds of the present disclosure are prepared by a Johnson Rearrangement of undecavertol, followed by reduction of the resulting ether.

The Claisen Rearrangement is a reaction known to those skilled in the art of organic synthesis. When an allylic alcohol is converted to a vinyl ether and treated with acid and heat, the vinyl ether rearranges to a 4-alkenal. There are several Claisen products already known for their use in the flavor and fragrance industry (Nowicki, Molecules 2000, 1033-1050). The Johnson Rearrangement is similar to the Claisen Rearrangement, where an allylic alcohol is converted to a 4-alkenoic ester.

For the Claisen Rearrangement, the allylic alcohol can be treated with various vinyl reagents to generate the vinyl ether intermediate, including but not limited to ethyl vinyl ether, butyl vinyl ether and isopropenyl methyl ether. The Claisen Rearrangement can be catalyzed by various acids, including but not limited to mercury diacetate, p-toluenesulfphonic acid, phosphoric acid, phenyl phosphonic acid, propionic acid, palladium diacetate, palladium ditriflate, and 1,10-phenanthroline complexes of palladium diacetate and palladium ditriflate. Sometimes a base is added, such as pyridine, triethyl amine or triethanolamine. The Claisen Rearrangement can be performed neat or in a solvent such as toluene or xylenes. See J. Chem. Soc. Perkin Trans. I 1985, page 817, GB1281813, J. Org. Chem. 2007, 72, 4250-4253 and J. Org. Chem. 1976, pages 3497-3505.

The Johnson Rearrangement can be performed on allyl alcohols with triethyl orthoacetate or trimethyl orthoacetate in a variety of acids, including but not limited to propionic acid, palladium diacetate, palladium ditriflate, and 1,10-phenanthroline complexes of palladium diacetate and palladium ditriflate. This reaction is typically done neat, with the orthoacetate acting as both reagent and solvent. See Flavour Fragr. J. 2011, pages 329-335 and J. Org. Chem. 1976, pages 3497-3505.

In certain embodiments, a compound of Formula (I) can be prepared by applying the Claisen Rearrangement to undecavertol. In certain embodiments, the compound of Formula (I), where R is hydrogen, can be prepared by applying Claisen Rearrangement to undecavertol. In certain embodiments, a compound of Formula (I) can be prepared by applying the Johnson Rearrangement to undecavertol to form an ester, e.g., where R is a $C_{1-2}$ alkoxy group. In certain embodiments, the compound of Formula (I), where R is an alkoxy group, can be prepared by applying Johnson Rearrangement to undecavertol. In certain embodiments, a compound of Formula (I) can be prepared by oxidation or hydrolysis of another compound of Formula (I). In certain embodiments, the compound of Formula (I), where R is hydrogen, can be oxidized to the carboxylic acid. In certain embodiments, the compound of Formula (I), where R is a hydroxy group, can also be made from the hydrolysis of the compounds of Formula (I) where R is an alkoxy group.

In certain embodiments, the compound of Formula (I), where R is hydrogen, being an aldehyde, can be reacted to make new compounds, such as the oximes and Schiff bases of Formula (II).

In certain embodiments, a compound of Formula (III) can be prepared from a compound of Formula (I). In certain embodiments, the compound of Formula (I), where R is hydrogen, can be reduced to form the compound of Formula (III), where R is a hydroxymethyl group. In certain embodiments, the compound of Formula (I), where R is a $C_{1-2}$ alkoxy group, can be reduced to form the compound of Formula (III), where R is a hydroxymethyl group. The resulting compound of either of the above reductions can be acetylated to prepare the compound of Formula (III), where R is a methyl ethanoate group.

In certain embodiments, the compound of Formula (I), where R is hydrogen, can be subjected to a Grignard reaction to produce the compound of Formula (III), where R is 1-ethanol. The Grignard reaction is known to those skilled in the art. In certain embodiments, a methyl Grignard reagent can be used to convert an aldehyde to a secondary alcohol. In certain embodiments, a compound of Formula (III) can be prepared from a compound of Formula (II). In certain embodiments, the oxime of Formula (II), where R is a hydroxy group, can be dehydrated to form the nitrile of Formula (III) where R is a cyano group.

In certain embodiments, a compound of Formula (IV) can be prepared from a compound of Formula (I). In certain embodiments, the compound of Formula (I), where R is hydrogen, can be hydrogenated to the fully saturated alcohol to produce the compound of Formula (IV), where R is a hydroxymethyl group. In certain embodiments, the compound of Formula (I), where R is hydrogen, can also be selectively hydrogenated to the saturated aldehyde to produce the compound of Formula (IV), where R is an aldehyde group.

Fragrance or Flavor Compositions

Any one of the above-described compounds can be included in a fragrance or flavor composition.

Fragrance Compositions

In certain embodiments, any one of the above described compounds can be provided in a fragrance composition.

Certain embodiments of the presently disclosed subject matter provide a method to modify, enhance or improve the odor properties of a fragrance composition by adding to the composition an effective quantity of one or more of the compounds of Formulas (I-IV).

The compounds of the present disclosure are particularly valuable as being capable of imparting violet notes to a fragrance composition. For fragrance applications, typical concentrations of the compounds of Formulas (I-IV) range from about 0.001% to about 20% by weight, preferably from about 0.01% to about 10% by weight, more preferably from about 0.1% to about 5%, and more preferably from about to 1% to about 3% based on the total weight of the composition into which the compound is incorporated. In other embodiments, the concentrations of the compounds of Formulas (I-IV) range from about 0.1% to about 8% by weight, or from about 0.1% to about 5% by weight, or from about 0.1% to about 4%, or from about 0.1% to about 3%, or from about 0.1% to about 2%, or from about 0.1% to about 1%, based on the total weight of the composition into which the fragrance compound is incorporated. Those skilled in the art are able to employ the desired level of the compounds of the disclosed subject matter to provide the desired fragrance/flavor and intensity. In general, compounds of the present disclosure can be used in relatively small amounts, typically via significant dilutions due to their high-impact, diffusive properties.

The compounds of the presently disclosed subject matter can be combined with one or more fragrance accords or compounds from various fragrance categories including but not limited to one or more aldehydic compound(s), one or more animalic compound(s), one or more balsamic compound(s), one or more citrus compound(s), one or more floral compound(s), one or more fruity compound(s), one or more gourmand compound(s), one or more green compound(s) one or more herbaceous compound(s) one or more marine compound(s), one or more mossy compound(s), one or more musk compound(s), one or more piney compound(s), one or more powdery compound(s), one or more spicy compound(s) and/or one or more woody compound(s), and combinations thereof.

Non-limiting examples of suitable aldehydic compounds include acetaldehyde C-8, acetaldehdye C-9, acetaldehyde C-10, adoxal, aldehyde C-8, aldehyde C-9, aldehyde C-10, aldehyde C-11, aldehyde C-12, aldehyde C-12 lauric, aldehyde C-12 MNA, aldehyde supra, cyclomyral trans-2-decenal, trans-4-decenal cis-4-decenal, 9-decenal, myrac aldehyde, precyclemone B, trans-2-decenal, undecylenic aldehyde, VERNALDEHYDE®, and combinations thereof.

Non-limiting examples of an animalic compound are AMBRETONE®, ambrettolide, ambrinol, ALDRON®, civet, p-cresol, indole, skatole, and combinations thereof.

Non-limiting examples of a balsamic compound are benzy salicylate, cylohexyl salicylate, isopropoxy ethyl salicylate, phenethyl salicylate, styrax oil, and combinations thereof.

Non-limiting examples of a citrus compound are delta-3-carene, citral, citronellal, L-citronellol, decanal, limonene, myrcenol, nootkatone, sinensal, bergamot oil, grapefruit oil, lemon oil, lime oil, orange oil tridecene-2-nitrile, and/or yuzu core base.

Non-limiting examples of a floral compound are acetanisole, alpha amyl cinnamaldehyde, anisyl acetate, anisic aldehyde, benzyl acetate, bourgeonal, butyl acetate, 1-citrol, cyclamen aldehyde, cyclohexyl lactone, delta-damascone, 9-decen-1-ol, dimethyl benzyl carbinol, farnesal, 1-dihydrofarnesal, 1-farnesal, farnesol, FLORHYDRAL®, floralozone, FLOROL®, geraniol, gernayl acetate, piperonal, HEDIONE®, heliobouquet, hexyl cinnamaldehyde, hexyl salicylate, indole, alpha-ionone, beta-ionone, isopropoxy ethyl salicylate, JASMODIONE®, cis-jasmone, KOVANOL®, LAURINAL®, lilial, linalool, linalyl acetate, LOREXAN®, magnolan, MAYOL®, methyl dihydrojasomante, gamma-methyl ionone, methoxymelonal, nerol, nerolione, neryl acetate, 2-pentyl cyclopentanone, PEONILE®, phenoxanol, phenoxy ethyl isobutyrate, phenylacetaldehyde, phenyl ethyl alcohol, rose oxide, rosephenone, SUZARAL®, terpineol, undecavertol, VELOUTONE®, yara yara, geranium oil, lavender oil, rose oil, ylang oil, and combinations thereof.

Non-limiting examples of a fruity compound are aldehyde C-16, allyl caproate, allyl cyclohexyl proprionate, allyl heptanoate, amyl acetate, benzaldehyde, CASSIS®, L-citronellyl acetate, L-citronellyl nitrile, CYCLACET®, CYCLAPROP®, damascenone, beta-decalactone, gamma-decalactone, diethyl malonate, dimethyl benzyl carbinol acetate, dimethyl phenyl ethyl carbinol, dimethyl sulfide, γ-dodecalactone, ethyl acetate, ethyl butyrate, ethyl caproate, ethyl decadienotate, ethyl-2-methylbutyrate, ethyl acetoacetate, ethyl propionate, FLOROL®, FRUITATE®, hexyl acetate, hexyl isobutyrate, isoamyl acetate, jasmolactone, manzanate, melonal, methyl heptyl ketone, gamma-nonalactone, gamma-octalactone, phenyl ethyl isobutyrate, raspberry ketone, RINGONOL®, THESARON®, tolyl aldehyde, γ-undecalactone, vanoris, verdox, and combinations thereof.

Non-limiting examples of a gourmand compound are butyl butyryl lactate, caprylic acid, coumarin, ethyl fraison, ethyl vanillin, ethyl maltol (e.g., Veltol Plus), filbertone, FURANEOL®, guaiacol, maple furanone, 2-acetyl pyrazine, 2,5-dimethyl pyrazine, vanillin, and combinations thereof.

Non-limiting examples of a green compound are allyl amyl glycolate, DYNASCONE®, galbanolene, trans-2-hexenal, cis-3-hexenol, hexen-1-ol, cis-3-hexenyl acetate, cis-3-hexenyl butyrate, cis-3-hexenyl formate, cis-3-hexenyl salicyclate, liffarome, 2-methoxy-2-methylheptane, methyl octine carbonate, neofolione, 2,6-nonadienal, OXANE®, SCENTENAL®, STEMONE®, styrallyl acetate, TRIPLAL®, undecavertol, violet methyl carbonate (e.g., violet T), vionil, violet leaf extract, and combinations thereof.

Non-limiting examples of a herbaceous compound are bamboo ketone, canthoxal, carvacrol, clary sage natural oil, DIMETOL®, natural basil oil, natural cedar leaf oil, and combinations thereof.

Non-limiting examples of a marine compound are Calone® 1951, floralozone, MARENIL®, MARITIMA®, myrac aldehyde, ultrazure, and combinations thereof.

Non-limiting examples of a mossy compound are hinokitiol, isobutyl quinolone, isopropyl quinolone and/or Oakmoss™ #1, and combinations thereof.

Non-limiting examples of a musk compound are ambrettolide, AMBRETONE®, AMBROXAN®, EXALTOLIDE®, GALAXOLIDE®, HABANOLIDE®, HELVETOLIDE®, (1'R)-3-methyl-5-(2,2,3-trimethylcyclopentan-1-yl)-2-pentanone, MUSCENONE®, musk T, L-muscone, TONALID®, and combinations thereof.

Non-limiting examples of a piney compound are 1-borneol, 1-bornyl acetate, camphene, dihydroterpineol, β-pinene, and combinations thereof.

Non-limiting examples of a powdery compound are heliotropine and/or whiskey lactone (methyl octalactone).

Non-limiting examples of a spicy compound are delta-caryophellene, cinnamaldehyde, cuminaldehyde, eugenol, isoeugenol, perilla aldehyde, cardamom oil, clove oil, ginger extract, black pepper extract and combinations thereof.

Non-limiting examples of a woody and/or amber compound are amber core, amber extreme, ambretol, AMBROCENIDE®, AMBROXAN®, bacdanol, boisambrene forte, cashmeran, cedramber, cedanol, EBANOL®, HINDINOL®, hinokitiol, dH-ionone beta, JAVANOL®, karanal, OKOUMAL®, ORBITONE®, patchouly oil, sandalwood, and combinations thereof.

In certain nonlimiting embodiments, the compound of Formula (I), where R is hydrogen, the compound can be used from about 0.1% to about 5% in a fragrance. More specifically, in a bar soap, the compound of Formula (I), where R is hydrogen, can be used from about 0.5% to about 5% in a fragrance, or from about 0.5% to about 1.5% in a fragrance, which is then used at up to about 1.5% in a bar soap. In another embodiment, in a candle, the compound of Formula (I), where R is hydrogen, can be used from about 1% to about 2%, in a fragrance, which is then used at up to about 3% in a candle. In another embodiment, in a shampoo, the compound of Formula (I), where R is hydrogen, can be used from about 0.1% to about 5%, but most often used at about 1% to about 2% in a fragrance. The compound of Formula (I), where R is hydrogen, can also be use in a fine fragrance from about 0.1% to about 1%, but most often used at about 0.2% in a fragrance.

The compounds of the presently disclosed subject matter can be combined with one or more fragrance compounds from various fragrance categories including but not limited to amber, citrus, floral, fruity, green, musky, spicy, and woody. The amounts of the fragrance compounds can vary depending on the intended resulting fragrance composition, but can range from about 0.1 parts per thousand to about 800 parts per thousand, or from about 1 part per thousand to about 500 parts per thousand.

The compounds of the disclosed subject matter provide unique and unexpected odor properties. For example, 3-ethyl-4-methyldec-4-enal was compared with the known fragrance ingredients neofolion (methyl 2-nonenoate) and undecavertol. Neofolion is light and fresh but a bit thin, with less volume than 3-ethyl-4-methyldec-4-enal. The odor of undecavertol is violet and aquatic, and less fruity than 3-ethyl-4-methyldec-4-enal.

Such compositions can contain or consist of at least one ingredient selected from a group consisting of a fragrance carrier and a fragrance base. Such compositions can also consist of at least one fragrance adjuvant.

Fragrance carriers can be a liquid or a solid, and typically do not significantly alter the olfactory properties of the fragrance ingredients. Some non-limiting examples of fragrance carriers include an emulsifying system, encapsulating materials, natural or modified starches, polymers, gums, pectins, gelatinous or porous cellular materials, waxes, and solvents which are typically employed in fragrance applications.

Fragrance base refers to any composition comprising at least one fragrance co-ingredient. In general, these co-ingredients belong to chemical classes such as, but not limited to: alcohols, aldehydes, ketones, esters, ethers, acetals, oximes, acetates, nitriles, terpenes, saturated and unsaturated hydrocarbons, and essential oils of natural or synthetic origins.

The fragrance compositions according to the disclosed subject matter can be in the form of a simple mixture of the various co-ingredients and solvents, or also in the form of a biphasic system, such as an emulsion or microemulsion. Such systems are well-known to persons skilled in the art.

The flavor compositions of the presently disclosed subject matter can further comprise one or more support materials. By way of non-limiting example, support materials can include diluents, e.g., ethanol, purified water, glycerol; solvents; carriers, e.g., propylene glycol, triacetin; preservatives, e.g., sulfites, sodium nitrite, propionic acid, sorbic acid, benzoic acid, disodium ethylenediaminetetraacetic acid (EDTA); flavoring agents, e.g., alcohols, esters, aldehydes; ketones, lactones, phenols, flavor enhancers, e.g., monosodium glutamate (MSG), monopotassium glutamate, calcium diglutamate (CDG), guanosine monophosphate disodium guanylate, sodium guanylate, inosinic acid and its salts, L-leucine; antioxidants, e.g., ascorbic acid, sodium ascorbate, fatty acid esters of ascorbic acid, tocopherols, alpha-tocopherol, gamma-tocopherol, delta-tocopherol, propyl gallate, octyl gallate, erythorbic acid, sodium erythorbate, dodecyl gallate, tertiary-butyl hydroquinone (TBHQ), butylated hydroxyanisole (BHA), butylated hydroxytoluene (BHT), citric acid, 4-hexylresorcinol; color retention agents; dyes or lakes; sequestrants, emulsifiers, e.g., lecithins, monoglyceride, acetylated monoglyceride, lactylated monoglyceride, sugar ester, sorbitan ester, polyglycerol ester, calcium stearoyl di laciate; stabilizers; acids, bases, and/or anticaking agents, e.g., calcium silicate, magnesium carbonate, sodium aluminosilicate.

Suitable consumer products that can include a fragrance compound or fragrance composition of the presently disclosed subject matter include but are not limited to: 1) air care products, e.g., candles, air fresheners; 2) fine fragrances; 3) personal care products, e.g., soaps, deodorants, adult and baby shampoos, conditioners, shower gels, shaving lotions, infant and toddler care wipes; 4) cosmetics, e.g., lotions, creams and ointments for the skin, color cosmetics; 5) fabric and home care products, e.g., laundry detergents, fabric softeners and conditioners, rinse additives; dish detergents, household and institutional cleansers/cleaning agents; 6) pharmaceutical and over-the-counter (OTC) products, e.g., medicated soaps, medicated shampoos, medicated skin care products; and 7) insect repellents or insecticides. Depending on the solvents that can be present in some end products, it can be necessary to protect the compounds from premature degradation, for example by encapsulation or with a stabilizer, or other methods well-known to those of ordinary skill in the art.

The above-listing of end products is non-limiting. The compositions of the presently disclosed subject matter can be included in a number of additional products. Non-limiting examples of fine fragrance products include eau de perfume, eau de toilet, eau de cologne, and the like.

Non-limiting examples of cosmetics include skin-care cosmetics, face washing creams, varnishing creams, cleansing creams, cold creams, massage creams and oils, milky lotions, skin toning lotion, makeup remover, makeup cosmetics, foundations, face powders, pressed powders, talcum powders, lip sticks, lip creams, cheek powders, eyeliners, mascara, eye shadows, eyebrow pencils, eye packs, nail enamels, nail enamel removers, suntan products, sunscreen products, and the like.

Non-limiting examples of hair care products include pomades, rinses, brilliantines, setting lotions, hair sticks, hair solids, hair oils, hair treatments, hair creams, hair tonics, hair liquids, hair sprays, hair restorers, hair dyes, permanent wave lotions, and the like.

Non-limiting examples of personal care products include antiperspirants, after-shave lotions and gels, bath soaps, perfumed soaps, transparent soaps, synthetic soaps, body shampoos, hand soaps, bath salts, bath tablets, bath liquids, foam and bubble baths, bath oils, bath perfumes, bath capsules, milk baths, bath gels, bath cubes, and the like.

Non-limiting examples of laundry care products include heavy duty detergents for clothes, light duty detergents for clothes, liquid detergents, laundering soaps, compact detergents, powder soaps, softening finishing agents, and softeners.

Non-limiting examples of home care products include furniture care products, car care products and the like; insect repellent, insecticides, and the like Flavor Compositions In certain embodiments, any one of the above-described compounds can be provided in a flavor composition. Certain embodiments of the presently disclosed subject matter provide a method to modify, enhance or improve the taste properties of a flavor composition by adding to the composition an effective quantity of one or more of the compounds of Formulas (I-IV).

Those skilled in the art are able to employ the desired level of said compounds to provide the desired flavor and intensity. Much higher concentrations can be employed when the compounds are used in concentrated flavors and flavor compositions. For flavor applications, concentrations of compounds of Formulas (I-IV) are based on the total weight of the composition into which the fragrance compound is incorporated. For flavor applications, typical concentrations of the compounds of Formulas (I-IV) range from about 0.001% to about 20% by weight, preferably from about 0.01% to about 10% by weight, more preferably from about 0.1% to about 5%, and more preferably from about to 1% to about 3% based on the total weight of the composition into which the compound is incorporated. Those skilled in the art are able to employ the desired level of said compound to provide the desired flavor and intensity. Much higher concentrations can be employed when the compound is used in concentrated flavors and flavor compositions.

As used herein, organoleptic effective quantity will be defined as the amount of said compound in a flavor composition in which the individual component will contribute its characteristic flavor properties. However, the organoleptic effect or taste profile of the flavor composition will be the sum of the effects of all flavor ingredients present. Therefore, the compounds embodied in the presently disclosed subject matter can be employed in more complex flavor compositions comprising one or more other flavor ingredients, or other flavor compositions, to modify the overall taste characteristics of the flavor composition via their own organoleptic properties or through enhancing or complimenting the contributions of the other flavor ingredient(s) present within the said composition. Such other flavor ingredients or flavor compositions include, for example, natural or synthetic flavors, i.e., fruit flavors (e.g., lemon, lime, orange, grapefruit; cherry, strawberry, raspberry, cranberry; apple, grape, pineapple, banana, tomato); natural or synthetic botanical flavors (e.g., tea flavors, coffee flavors, hazelnut, almond, pecan or other nut flavors; vanilla flavors), and flavor compositions with complex flavor profiles (e.g., cola flavors or imagined flavors, such as "birthday cake" or "ice cream sundae"). The quantity of the presently disclosed compound in such more complex flavor compositions will vary widely depending on the presence of other ingredients present, their relative amounts, the desired taste profile, and the nature of the consumer product in which the flavor composition will be utilized.

The flavor carrier can be a liquid or a solid, and typically does not significantly alter the olfactory or organoleptic properties of the flavor ingredients, respectively. Some non-limiting examples of flavor carriers include an emulsifying system, encapsulating materials, natural or modified starches, polymers, pectins, proteins, polysaccharides, gums and solvents which are typically employed in flavor applications.

The flavor compositions according to the disclosed subject matter can be in the form of a simple mixture of the various co-ingredients, adjuvants, and solvents, or also in the form of a biphasic system such as an emulsion or microemulsion. Such systems are well-known to persons skilled in the art.

The flavor compositions of the presently disclosed subject matter can further comprise one or more support materials. By way of non-limiting example, support materials can include diluents, e.g., ethanol, purified water, glycerol; solvents; carriers, e.g., propylene glycol, triacetin; preservatives, e.g., sulfites, sodium nitrite, propionic acid, sorbic acid, benzoic acid, disodium ethylenediaminetetraacetic acid (EDTA); flavoring agents, e.g., alcohols, esters, aldehydes; ketones, lactones, phenols, flavor enhancers, e.g., monosodium glutamate (MSG), monopotassium glutamate, calcium diglutamate (CDG), guanosine monophosphate disodium guanylate, sodium guanylate, inosinic acid and its salts, L-leucine; antioxidants, e.g., ascorbic acid, sodium ascorbate, fatty acid esters of ascorbic acid, tocopherols, alpha-tocopherol, gamma-tocopherol, delta-tocopherol, propyl gallate, octyl gallate, erythorbic acid, sodium erythorbate, dodecyl gallate, tertiary-butyl hydroquinone (TBHQ), butylated hydroxyanisole (BHA), butylated hydroxytoluene (BHT), citric acid, 4-hexylresorcinol; color retention agents; dyes or lakes; sequestrants, emulsifiers, e.g., lecithins, monoglyceride, acetylated monoglyceride, lactylated monoglyceride, sugar ester, sorbitan ester, polyglycerol ester, calcium stearoyl di laciate; stabilizers; acids, bases, and/or anticaking agents, e.g., calcium silicate, magnesium carbonate, sodium aluminosilicate.

As used herein, the terms "consumer product" and "end product" relate to end use materials that can encompass the flavor compound (i.e., compounds encompassed by Formulas (I-IV)) or flavor compositions of the presently disclosed subject matter may be used in consumer products such as foods or beverages, oral care products, animal feed and pet foods, and pharmaceuticals and over-the-counter medications. Examples of suitable consumer products include, but are not limited to carbonated fruit beverages, carbonated cola drinks, wine coolers, cordials, flavored water, powders for drinks (e.g., powdered sports or "hydrating" drinks), fruit based "smoothy" drinks, milk-based drinks, hard candy, soft candy, taffy, chocolates, sugarless candies, chewing gum, bubble gum, condiments, spices and seasonings, dry cereal, oatmeal, granola bars, condiments and preserves, soups, alcoholic beverages, energy beverages, juices, teas, coffees, salsa, gel beads, film strips for halitosis, gelatin candies, pectin candies, starch candies, lozenges, chewable tablets, breath mints, oral wash, tooth gel, cough drops, throat lozenges, throat sprays, toothpastes, mouth rinses, nicotine gums, decongestants, oral analgesics, indigestion preparations, and antacids.

The flavor compositions according to the disclosed subject matter can be in the form of a simple mixture of flavoring ingredients or in an encapsulated form, e.g., a flavoring composition entrapped into a solid matrix that can comprise wall-forming and plasticizing materials such as mono-, di-, or trisaccharides, natural or modified starches, hydrocolloids, cellulose derivatives, polyvinyl acetates, polyvinylalcohols, proteins, or pectins. Examples of particularly useful matrix materials include, for example, sucrose, glucose, lactose, levulose, fructose, maltose, ribose, dextrose, isomalt, sorbitol, mannitol, xylitol, lactitol, maltitol, pentatol, arabinose, pentose, xylose, galactose, maltodextrin, dextrin, chemically modified starch, hydrogenated starch hydrolysate, succinylated or hydrolysed starch, agar, carrageenan, gum arabic, gum accacia, tragacanth, alginates, methyl cellulose, carboxymethyl cellulose, hydroxyethyl cellulose, hydroxypropylmethyl cellulose, derivatives, gelatin, agar, alginate, and mixtures thereof. Encapsulation is well-known to persons skilled in the art, and can be performed, for instance, using techniques such as spray-drying, agglomeration or extrusion, or coating encapsulation, including coacervation and complex coacervation techniques.

In one embodiment, a compound of the presently disclosed subject matter is included/used in chewing and bubble gums and confectionaries (e.g., hard or soft candies or lozenges). Chewing gum compositions typically include one or more gum bases and other standard components such as flavoring agents, softeners, sweeteners, and the like. Flavoring agents for use in chewing gum compositions are well known and include natural flavors such as citrus oils, peppermint oil, spearmint oil, oil of wintergreen, natural menthol, cinnamon, ginger and the like; artificial flavors such as menthol, carvone, limonene, cinnamic aldehyde, linalool, geraniol, ethyl butyrate, and the like. As is known in the art, the ingredients used in chewing gum compositions can include sweeteners, both natural and artificial and both sugar and sugarless. Sweeteners are typically present in the chewing gum compositions in amounts of from about 20% to 80% by weight, preferably from about 30% to 60% by weight, based on the total weight of the chewing gum composition. Sugarless sweeteners include, but are not limited sugar alcohols such as Sorbitol, manifold, xylitol, hydrogenated starch hydrolysates, malitol, and the like. High intensity sweeteners such as sucralose, aspartame, neotame, salts of acesulfame, and the like, when employed, are typically present up to about 1.0% by weight.

In an alternative embodiment, a compound of the presently disclosed subject matter is included in an oral personal care product (e.g., a mouthwash, toothpaste, mouth cleaners, troches, chewing gums, and the like). For example, a mouthwash can be prepared by dissolving a flavor composition (e.g., a flavor cocktail) (liquid or powder) that includes a compound of the presently disclosed subject matter in a solvent (e.g., water) that further includes, for example, a flavor such as menthol and a surfactant; and then mixing the resulting solution with, for example, an aqueous erythritol solution.

In one embodiment of the presently disclosed subject matter, a compound of the presently disclosed subject matter is added, directly or indirectly, to a pharmaceutical dosage form (e.g., a tablet, capsule, drop, or lozenge) that contains a therapeutically active agent (e.g., a medicament). For example, one embodiment of the presently disclosed subject matter provides a cough drop or lozenge containing one or more compounds of the present disclosure and, optionally, further containing menthol or other medicaments for the treatment of sore throat, coughing or other upper respiratory ailments.

One or more of the present compounds can also be added to, for example, compositions for the preparation of: 1) carbonated or non-carbonated fruit beverages, carbonated cola drinks, wine coolers, fruit liquors, cordials, milk drinks, smoothy drinks, flavored water, tropical alcoholic and "virgin" drink mixes (e.g., margarita, piña colada or "rum-runner" concentrates), and powders for drinks (e.g., powdered sports or "hydrating" drinks); 2) frozen confectioneries such as ice creams, sherbets, and ice-lollies; hard candies, soft candies, taffies, chocolates, and sugarless candies; 3) desserts such as jelly and pudding; 4) confectioneries such as cakes, cookies, chewing gums, and bubble gums; 5) condiments, spices and seasonings, dry cereals, oatmeals, and granola bars; 6) alcoholic beverages, energy beverages, juices, teas, coffees, salsa, and gel beads; 7) film strips for halitosis, and oral personal care products; 8) gelatin candies, pectin candies, starch candies, lozenges, cough drops, throat lozenges, throat sprays, and toothpastes.

The present compounds can also be added to, for example; 1) Japanese confectioneries such as buns with bean-jam filling, bars of sweet jellied bean paste, and sweet jellied pounded rice; 2) jams; candies; 3) breads; 4) beverages such as green tea, oolong tea, black tea, persimmon leaf tea, Chamomile tea, *Sasa veitchii* tea, mulberry leaf tea, *Houttuynia cordata* tea, Puer tea, Mate tea, Rooibos tea, Gimunema tea, Guava tea, coffee, espresso, and hot and cold espresso and coffee products obtained by mixing espresso and/or coffee with milk, water or other liquids suitable for oral consumption (e.g., lattes, cafe au lait, cafe mocha), and cocoa; 5) soups such as Japanese flavor soup, western flavor soup, and Chinese flavor soup; 6) seasonings; 7) various instant beverages and foods; 8) various snack foods; and 9) other compositions for oral use.

EXAMPLES

The present application is further described by means of the examples, presented below, wherein the abbreviations have the usual meaning in the art.

The use of such examples is illustrative only and in no way limits the scope and meaning of the disclosed subject matter or of any exemplified term. Likewise, the disclosed subject matter is not limited to any particular preferred embodiments described herein. Indeed, many modifications and variations of the disclosed subject matter are apparent to those skilled in the art upon reading this specification. The disclosed subject matter is therefore to be limited only by the terms of the appended claims along with the full scope of equivalents to which the claims are entitled.

The following Examples are provided as specific embodiments of the present invention, wherein the abbreviations have the usual meaning in the art. The temperatures are indicated in degrees centigrade (° C.); the NMR spectral data were recorded in $CDCl_3$ with a 500 MHz machine for $^1H$ and $^{13}C$, the chemical displacements are indicated in ppm with respect to TMS as the standard.

Example 1: Synthesis of 3-ethyl-4-methyldec-4-enal 3-ethyl-4-methyldec-4-enal was synthesized as shown in Examples 1-A and 1-B below:

Example 1-A

Undecavertol (3 g), ethyl vinyl ether (22.6 mL, 13.4 eq.), mercuric acetate (5.3 g, 0.95 eq.) and toluene (50 mL) were combined under $N_2$ gas and refluxed for 18 hours. Another 7.6 mL (4.5 eq.) of ethyl vinyl ether and an additional 50 mL toluene were then added and reflux continued for 5 hours.

The reaction was cooled, and acetic acid (1 mL) was added and stirred at room temperature for 30 minutes. The mixture was extracted with diethyl ether and washed with 5% KOH, dried over MgSO$_4$, filtered and concentrated. The crude product was purified by column chromatography (2% ethyl acetate in hexanes) to give the product as a mixture of its isomers (1.7 g; 41% yield). GC/MS(EI): m/z (%) 196 (M$^+$, 2), 181 (4), 167 (3), 152 (53), 125 (48), 111 (41), 95 (66), 81 (60), 69 (99), 55 (100), 41 (99). $^1$H NMR (CDCl$_3$): δ 9.62 (C$\underline{H}$O). $^{13}$C NMR (CDCl$_3$): δ 203.1 and 202.7 ($\underline{C}$HO).

Example 1-B

Undecavertol (50 g), ethyl vinyl ether (67.6 mL, 2.4 eq.), phenyl phosphonic acid (0.5, 0.01 eq.) and toluene (50 mL) were sealed in an autoclave. The vessel was purged with N$_2$ gas, then heated to 150° C. over 30 minutes. Then the temperature was raised to 180° C., at which point the pressure inside the vessel rose to 8 bar. After 2 hours, the reaction was complete. The product (31.5 g) was isolated as a mixture of its isomers by distillation (2T, 100° C.); 54.6% yield. GC/MS(EI): m/z (%) 196 (M$^+$, 2), 181 (4), 167 (3), 152 (53), 125 (48), 111 (41), 95 (66), 81 (60), 69 (99), 55 (100), 41 (99). $^1$H NMR (CDCl$_3$): δ 9.62 (C$\underline{H}$O). $^{13}$C NMR (CDCl$_3$): δ 203.1 and 202.7 ($\underline{C}$HO). Odor: aldehydic, violet, floral, green, aquatic, citrus, mandarin, lime.

Example 2: Synthesis of Ethyl 3-ethyl-4-methyldec-4-enoate

Ethyl 3-ethyl-4-methyldec-4-enoate was synthesized according to the following method:
Undecavertol (8.3 g), triethyl orthoacetate (44.5 mL, 5 eq.), and propionic acid (0.36 mL, 0.1 eq.) were heated to 180° C. in a roundbottom flask equipped with a Dean-Stark apparatus for 24 hours. The mixture was distilled to remove ethanol and remaining triethyl orthoacetate (10T, 85° C.), leaving 7.1 g of crude product as a mixture of a its isomers. This was further purified by column chromatography (2% ethyl acetate in hexanes) to give 4.3 g of the pure product as a mixture of its isomers (36.6 isolated % yield). GC/MS(EI): m/z (%) 240 (M$^+$, 11), 225 (1), 211 (4), 195 (7), 183 (3), 170 (5), 152 958), 137 (12), 123 (24), 109 (38), 95 (75), 81 (56), 69 (71), 55 (98), 41 (98). Odor: fruity, violet.

Example 3: Synthesis of 3-ethyl-4methyldec-4-enal oxime 3-ethyl-4methyldec-4-enal oxime was synthesized according to the following method:
The compound of Example 1 (20 g) was added to a mixture of hydroxylamine-hydrochloride (12.05 g, 1.7 eq.), pyridine (16.1 g, 2 eq.) and ethanol (400 mL) and heated at a bath temperature of 90° C. for 18 hours. After cooling, the ethanol was removed under reduced pressure. The reaction mixture was diluted with ethyl acetate and quenched with H$_2$O. The organics were washed with 1N HCl and brine, and then dried over MgSO$_4$. After filtering, the solvent and pyridine were removed under reduced pressure. Kugelrohr distillation (0.5T, 106° C.) provided 16.9 g of the product as a mixture of its isomers (78.6% yield). GC/MS(EI): m/z (%) 211 (M$^+$, 1), 194 (14), 179 (14), 166 (7), 152 (10), 140, (12), 124 (13), 109 (16), 97 (32), 83 (40), 69 (58), 55 (100), 41 (60). Odor: violet, fig, sugar snap peas, vegetable.

Example 4: Synthesis of Methyl 2-((3-ethyl-4-methyldec-4-enylidene)amino)benzoate Methyl 2-((3-ethyl-4-methyldec-4-enylidene)amino)benzoate was synthesized according to the following method:

The compound of Example 1 (2 g) was heated under vacuum (100T) with methyl anthranilate (1.5 g, 1.0 eq.) slowly up to 145° C. When most of the product was generated, the temperature was lowered to 100° C., and the pressure to 0.2T. to remove any remaining starting materials. The pure product (1.5 g) was obtained as a mixture of its isomers (45.5% yield). GC/MS(EI): m/z (%) 329 (M$^+$, 1), 300 (1), 198 (2), 177 (3), 167 (2), 158 (3), 146 (3), 132 (6), 119 (6), 105 (4), 91 (12), 77 (23), 67 (14), 55 (41), 41 (100). $^1$H NMR (CDCl$_3$): δ 3.85 (3H, s). Odor: fruity, green, slightly aquatic, violet, floral, buttery, milky, mimosa.

Example 5: Synthesis of 3-ethyl-4-methyldec-4-en-1-ol 3-ethyl-4-methyldec-4-en-1-ol was synthesized according to the following method:
The compound of Example 1 (17 g) was combined with methanol (80 mL) and cooled on a bath at 8° C. NaBH$_4$ pellets were added over 2 hours, keeping the temperature below 15° C. When the reaction was complete it was quenched while cold with water, and allowed to warm gradually to room temperature. The methanol was removed under vacuum and the remaining mixture extracted with diethyl ether. After concentration of the organic extracts, the crude product was distilled by Kugelrohr (0.2T, 85° C.) to give 15.4 g of the product as a mixture of isomers (89.7% yield). GC/MS(EI): m/z (%) 198 (M$^+$, 8), 183 (10), 154 (47), 129 (20), 113 (99), 95 (69), 84 (97), 69 (98), 55 (100), 43 (98). Odor: oily, fruity, vegetal, floral, avocado.

Example 6: Synthesis of 3-ethyl-4-methyldec-4-enyl Acetate 3-ethyl-4-methyldec-4-enyl acetate was synthesized according to the following method:
The compound of Example 5 (17 g) was combined with methanol (80 mL) and cooled on a bath at 8° C. NaBH$_4$ pellets were added over 2 hours, keeping the temperature below 15° C. When the reaction was complete it was quenched while cold with water, and allowed to warm gradually to room temperature. The methanol was removed under vacuum and the remaining mixture extracted with diethyl ether. After concentration of the organic extracts, the crude product was distilled by Kugelrohr (0.2T, 85° C.) to give 15.4 g of the product as a mixture of isomers (89.7% yield). $^1$H NMR (CDCl$_3$): δ 5.12 (1H, vinyl), 2.01 (3H, s). $^{13}$C NMR (CDCl$_3$): δ 135.6 and 127.8 ($\underline{C}$=$\underline{C}$). Odor: fruity, leafy, medicinal.

Example 7: Synthesis of 4-ethyl-5-methylundec-5-en-2-ol 4-ethyl-5-methylundec-5-en-2-ol was synthesized according to the following method:
The compound of Example 1 (10 g) with 20 mL of anhydrous diethyl ether was added dropwise to methylmagnesium bromide (3M, 20.4 mL, 1.2 eq.) at room temperature. After 12 hours of stirring, the reaction was cooled on ice, quenched with saturated NH$_4$Cl and extracted with diethyl ether. The resulting emulsion was filtered and washed with ether. The filtrate was concentrated and distilled by Kugelrohr (0.3T, 76° C.) to give 9 g of the desired product as a mixture of isomers (83.3% yield). GC/MS(EI): m/z (%) 212 (M$^+$, 1), 197 (3), 179 (2), 165 (4), 154 (36), 137 (6), 127 (45), 111 (35), 95 (42), 84 (90), 69 (96), 55 (100), 43 (91). $^1$H NMR (CDCl$_3$): δ 5.23 (1H, vinyl), 3.76 (1H, m).

$^{13}$C NMR (CDCl$_3$): δ 134.7 and 127.4 (C═C). Odor: grapefruit, hay, tea, alfalfa leaf.

Example 8: Synthesis of 3-ethyl-4-methyldec-4-enenitrile 3-ethyl-4-methyldec-4-enenitrile was synthesized according to the following method:

The compound of Example 3 (11 g) was refluxed in 1.1 g of K$_3$PO$_4$ and xylenes (66 mL) for 18 hours while H$_2$O generated was collected in a Dean-Stark trap. Upon completion, the reaction was quenched with H$_2$O, extracted with ethyl acetate and washed with brine. After drying over MgSO$_4$, filtering and concentrating under reduced pressure, the crude material was Kugelrohr distilled (0.8T, 104° C.) to give 7.7 g of the product as a mixture of its isomers (76.3% yield). GC/MS(EI): m/z (%) 193 (M$^+$, 10), 178 (9), 164 (12), 152 (31), 137 (20), 123 (40), 111 (46), 95 (60), 83 (95), 69 (99), 55 (100), 41 (99). Odor: fresh, herbaceous, ozonic, anisic, jasmone effect, apricot, pear, woody.

Example 9: 3-ethyl-4-methyldecan-1-ol 3-ethyl-4-methyldecan-1-ol was synthesized according to the following method:

The compound of Example 1 (5 g) was combined with 5% Pd/C (0.2 g) and ethanol (10 mL) in an autoclave under H$_2$ (400 psi) and heated to 100° C. for 12 hours. The mixture was then filtered through celite and concentrated by rotary evaporator. The crude product was distilled by Kugelrohr (0.3T, 99° C.) to give 4.4 g of product (85.5% yield). GC/MS(EI): m/z (%) 182 (M$^+$-18, 19), 167 (1), 154 (92), 140 (2), 126 (18), 111 (89), 97 (55), 84 (98), 69 (99), 55 (100), 41 (99). $^1$H NMR (CDCl$_3$): δ 3.63 (2H, m). $^{13}$C NMR (CDCl$_3$): δ 62.0 (CH$_2$OH). Odor: green, oily.

Example 10: Synthesis of 3-ethyl-4-methyldecanal 3-ethyl-4-methyldecanal was synthesized according to the following method:

The compound of Example 1 (1 g) was combined with 5% Pd/C (0.08 g) and cyclohexanes (10 mL) in an autoclave under H$_2$ (300 psi) at 25° C. for 12 hours. The mixture was then filtered through celite and concentrated by rotary evaporator. The crude product was subject to column chromatography (2% ethyl acetate in hexanes) to separate the aldehyde from the saturated alcohol to give 0.34 g of the product (33.6% yield). GC/MS(EI): m/z (%) 198 (M$^+$-18, 19), 167 (1), 154 (92), 140 (2), 126 (18), 111 (89), 97 (55), 84 (98), 69 (99), 55 (100), 41 (99). $^1$H NMR (CDCl$_3$): δ 9.74 (1H, s). $^{13}$C NMR (CDCl$_3$): δ 203.7 (CHO). Odor: savory, fresh parsley, aromatic green herbs.

Example 11

The compound of Formula (I), where R is hydrogen, was compared to the known fragrance material, undecavertol (4-methyl-3-decen-5-ol), for its violet, floral character. Specifically, the compound of Formula (I), where R is hydrogen, was compared to undecavertol used in a candle, as shown in the following example. 5% of the fragrance was added to the candle base.

A "Pink Mimosa" perfume composition with a floral violet note was prepared from the compound of Formula (I), where R is hydrogen, to demonstrate its use in a candle. The composition is provided in Table 1. The candle was evaluated by two Perfumers and one Evaluator, before burning and during burning.

TABLE 1

| FRAGRANCE CATEGORY | PARTS PER THOUSAND |
|---|---|
| Compound of Formula (I), R = H Uniquely violet floral Green/Floral/Fruity | 20 |
| Amber | 6 |
| Citrus | 124 |
| Floral | 451.4 |
| Fruity | 32.6 |
| Green | 3 |
| Musky | 100 |
| Spicy | 1 |
| Woody | 262 |
| Total | 1000 |

This composition using 20 ppt of the compound of Formula (I), where R is hydrogen, showed superior character and strength over the same composition substituted with 20 ppt of undecavertol. When undecavertol is used in this fragrance, it becomes harsh upon burning the candle, and develops a burnt, fishy, oily, and rubbery odor. When the compound of Formula (I), where R is hydrogen, is used in its stead, the odor is fresh, clean, and remains so upon burning. There are no oily and burnt notes, but more natural floral, violet notes.

Example 12

A chypre fruity perfume composition with a green fruity note was prepared from the compound of Formula I, where R═H, to demonstrate in a shampoo. The composition is provided in Table 2. The shampoo with and without the compound of Formula I, where R═H, was evaluated by two Perfumers and one Evaluator.

TABLE 2

| CATEGORY | PARTS PER THOUSAND |
|---|---|
| Citrus | 38 |
| Floral | 600 |
| Fruity | 81 |
| Gourmand | 75 |
| Marine | 40 |
| Moss | 1.3 |
| Musk | 65 |
| Woody | 4.7 |
| Solvent | 75 |
| Compound of Formula I where R = H Green/Floral/Fruity | 20 |
| Total | 1000 |

The fragrance was dosed at 0.5% in the shampoo with and without the compound of Formula I, where R═H. This composition using 20 ppt of the compound of Formula I, where R═H, gives more fruity, green apple notes, and also gives more volume compared to the version without the compound of Formula I, where R═H.

Example 13

A powdery floral perfume composition with a fresh green accent was prepared from the compound of formula I, where R=H, to demonstrate in a shampoo. The composition is provided in Table 3. The shampoo with and without the compound of formula I, where R=H, was evaluated by two Perfumers and one Evaluator.

TABLE 3

| CATEGORY | PARTS PER THOUSAND |
|---|---|
| Amber | 9 |
| Citrus | 5 |
| Floral | 561 |
| Fruity | 137 |
| Gourmand | 44 |
| Musk | 126 |
| Woody | 108 |
| Compound of Formula I where R = H Green/Floral/Fruity | 10 |
| Total | 1000 |

The fragrance was dosed at 0.5% in the shampoo with and without the compound of Formula I, where R=H. The composition using 10 ppt of the compound of Formula I, where R=H, gives more fresh, green fruity notes, and also gives more volume compared to the version without the compound of formula I, where R=H.

Although the presently disclosed subject matter and its advantages have been described in detail, it should be understood that various changes, substitutions and alterations can be made herein without departing from the spirit and scope of the application as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the presently disclosed subject matter, processes, machines, manufacture, compositions of matter, means, methods, or steps, presently existing or later to be developed that perform substantially the same function or achieve substantially the same result as the corresponding embodiments described herein can be utilized according to the presently disclosed subject matter. Accordingly, the appended claims are intended to include within their scope such processes, machines, manufacture, compositions of matter, means, methods, or steps.

In addition to the various embodiments depicted and claimed, the disclosed subject matter is also directed to other embodiments having any other possible combination of the features disclosed and claimed herein. As such, the particular features presented herein can be combined with each other in other manners within the scope of the disclosed subject matter such that the disclosed subject matter includes any suitable combination of the features disclosed herein. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the device, method, and system of the disclosed subject matter without departing from the spirit or scope of the disclosed subject matter. Thus, it is intended that the disclosed subject matter include modifications and variations that are within the scope of the appended claims and their equivalents.

For any patents, patent applications, publications, product descriptions, and protocols are cited throughout this application, the disclosures of all of which are incorporated herein by reference in their entireties for all purposes.

The invention claimed is:

1. A compound represented by Formula (I),

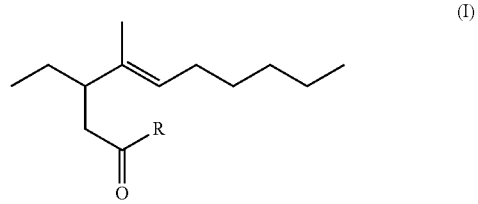

wherein R is hydrogen, a hydroxy group, or a $C_{1-2}$ alkoxy group.

2. A compound represented by Formula (II),

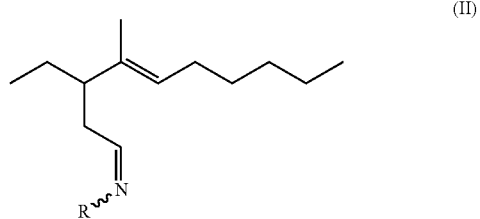

wherein R is a hydroxy group, a $C_{1-2}$ alkoxy group, an acetoxy group, 2-methylbenzoyl, or 2-ethylbenzoyl.

3. A compound represented by Formula (III),

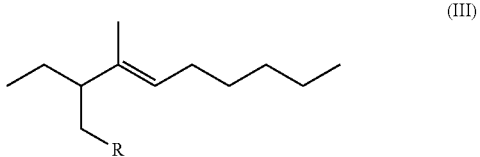

wherein R is a hydroxymethyl group, a methyl ethanoate group, 1-ethanol, or a cyano group.

4. A fragrance or flavor composition comprising one or more compounds of claim 1.

5. A consumer product containing the flavor or fragrance composition of claim 4.

6. A fragrance or flavor composition comprising one or more compounds of claim 2.

7. A fragrance or flavor composition comprising one or more compounds of claim 3.

8. A consumer product containing the flavor or fragrance composition of claim 6.

9. A consumer product containing the flavor or fragrance composition of claim 7.

* * * * *